United States Patent
Skinner

(10) Patent No.: US 7,276,026 B2
(45) Date of Patent: *Oct. 2, 2007

(54) METHOD AND SYSTEM FOR DETECTING AND/OR PREDICTING CEREBRAL DISORDERS

(75) Inventor: James Skinner, Bangor, PA (US)

(73) Assignee: Nonlinear Medicine, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/767,861

(22) Filed: Jan. 29, 2004

(65) Prior Publication Data

US 2004/0225202 A1 Nov. 11, 2004

Related U.S. Application Data

(63) Continuation-in-part of application No. 10/353,849, filed on Jan. 29, 2003, now Pat. No. 7,076,288.

(60) Provisional application No. 60/445,495, filed on Feb. 6, 2003.

(51) Int. Cl.
*A61B 5/00* (2006.01)

(52) U.S. Cl. ..................................... 600/300

(58) Field of Classification Search ................ 600/509, 600/544, 545, 300; 435/7.9; 128/920
See application file for complete search history.

(56) References Cited

U.S. PATENT DOCUMENTS 4,215,697 A * 8/1980 Demetrescu ................ 600/544
5,215,099 A 6/1993 Haberl et al.
5,482,045 A 1/1996 Rust et al.
5,709,214 A 1/1998 Skinner
5,720,294 A 2/1998 Skinner
2003/0104493 A1 6/2003 Ortel et al.

OTHER PUBLICATIONS

"Low-Dimensional Chaos In Event-Related Brain Potentials," by Molnar et al., *Internat. J. of Neuroscience*, 1992, vol. 66, pp. 263-276.
"Is The Heart Preadapted To Hypoxia? Evidence From Fractal Dynamics Of Heartbeat Interval Fluctuations At High Altitude," Meyer et al., *Integr. Physiol. Behav. Sci.*, 1998, vol. 33, pp. 9-40.
"Cerebral Autonomic Regulation Underlying Cardiovascular Disease," Skinner, James E., *Primer on the Autonomic Nervous System*, 1996, Chapt. 29, pp. 153-156.

(Continued)

*Primary Examiner*—George Manuel
(74) *Attorney, Agent, or Firm*—Needle & Rosenberg, P.C.

(57) ABSTRACT

Cerebral disorders are detected and/or predicted by analyzing input biological or physical data using a data processing routine. The data processing routine includes a set of application parameters associated with biological data correlating with the biological anomalies. The data processing routine uses an algorithm to produce a data series, e.g., a PD2i data series. The data series is used to detect or predict the onset of the cerebral disorders. To reduce noise in the data series, the slope is set to a predetermined number if it is less than a predetermined value. To further reduce noise, a noise interval within the data series is determined and, if the noise interval is within a predetermined range, the data series is divided by another predetermined number, and new values are produced for the data series.

25 Claims, 7 Drawing Sheets

OTHER PUBLICATIONS

"Introducing Chaos," Wolf, Stewart, *Integrative Physiological and Behavioral Science*, Jul.-Sep. 1994, vol. 29, No. 3, pp. 203-204.

"Estimating Fractal Dimension," Theiler, James, Aug. 30, 1989.

Takens, F., "On The Numerical Determination Of The Dimension Of An Attractor, Dynamical Systems And Bifurications," Groninger, 1984, vol. 1125 of *Lecture Notes In Mathematics*, Springer-Verlag, Berlin, 1985.

"Laser and brains: complex systems with low-dimensional attractors," *Dimensions and Entropies in Chaotic Systems*, 1985, pp. 231-240.

"Bohm's alternative to quantum mechanics," Albert, D.Z., *Scientific American*, May 1994, pp. 58-67.

"Strange attractors in the dynamics of brain activity," Babloyantz, A., *Complex Systems—operational approaches in neurobiology, physics, and computers*, 1985, pp. 116-122.

"Cognitive psychophysiology and human information processing," Donchin et al., *Psychophysiology: systems, processes and applications*, 1986, pp. 244-267.

"The Dimension of Chaotic Attractors," Farmer et al., *Physica D*, vol. 7D, Nos. 1-3, May 1983, pp. 153-180.

"Simulation of Chaotic EEG Patterns with a Dynamic Model of the Olfactory System," Freeman, *Biological Cybernetics*. vol. 56, 1987, pp. 139-150.

"Characterization of strange attractors," Grassberger et al., *Physical Review Letters*, 1983, vol. 50, No. 5, pp. 346-349.

"Direct Test for Determinism in a Time Series," Kaplan et al., *Physical Review Letters*, 1992, vol. 68, No. 4, pp. 427-430.

"Dimensional Analysis of Nonlinear Oscillations in Brain, Heart, and Muscle," Mayer-Kress et al., *Mathematical Biosciences*, 1988, 90, pp. 155-182.

"Localized Measures for Non-Stationary Time-Series of Physiological Data," Mayer-Kress et al., *Integrative Physiological and Behavioral Science*, Jul.-Sep. 1994, vol. 29, No. 3, pp. 205-210.

"Testing the Determinism of EEG and MEG," Mühlnickel et al., *Integrative Physiological and Behavioral Science*, vol. 29, No. 3, Jul.-Sep. 1994, pp. 262-269.

"Geometry from a Time Series," Packard et al., 1980, *The American Physical Society*, pp. 712-716.

"Long-range correlations in nucleotide sequences", Peng et al., *Nature*,1992, vol. 356, pp. 168-170.

"Approximate entropy as a measure of system complexity," Pincus, *Proc. Natl. Acad. Sci.*, vol. 88, Mar. 1991, pp. 2297-2301.

"Dynamics of brain electrical activity," Rapp et al., *Brain Topography*, 1989, vol. 2, pp. 99-118.

"A Guide to Dynamical Analysis," Rapp, *Integrative Physiological and Behavioral Science*, 1994, vol. 29, No. 3, pp. 311-327.

"Reconstruction expansion as a geometry-based framework for choosing proper delay times," Rosenstein et al., *Physica D*, 1994, vol. 73, pp. 82-98.

"Chaos in Physiology," Rossler et al., *Integrative Physiological and Behavioral Science*, Jul.-Sep. 1994, vol. 29, No. 3, pp. 328-333.

"Discriminating Deterministic versus Stochastic Dynamics in Neuronal Activity," Schiff et al., *Integrative Physiological and Behavioral Science*, Jul.-Sep. 1994, vol. 29, No. 3, pp. 246-261.

"How brains make chaos in order to make sense of the world," Skarda et al., *Cambridge University Press* (1987), pp. 161-195.

"Correlation Dimension of Heartbeat Intervals Is Reduced in Conscious Pigs by Myocardial Ischemia," Skinner et al., *Circulation Research* (1991), vol. 68, No. 4, pp. 966-976.

"On the Numerical Determination of the Dimension of an Attractor," Takens, 1984, Lecture Note in Mathematics, 1125, pp. 99-106.

"Spurious dimension from correlation algorithms applied to limited time-series data," Theiler, *Physical Review A*, 1986, vol. 34, No. 3, pp. 2427-2432.

"Testing for nonlinearity in time series: the method of surrogate data," Theiler et al., *Physica D*, vol. 58, pp. 77-94.

"Anatomical and Physiological Substrates of Event-Related Potentials," Wood et al., *Neurophysiology and Methodology*, 1984, pp. 681-721.

"Cryoblockade in limbic brain (amygdale) delays or prevents ventricular fibrillation following coronary artery occlusion in psychologically stressed pigs," Skinner et al., *Cir. Res.*, vol. 70, pp. 600-606, 1992.

"Low-dimensional chaos maps learning in a model neuropil (olfactory bulb)," Skinner et al., *Integrative Physiological and Behavioral Science*, Oct.-Dec. 1992, vol. 27, No. 4, pp. 304-322.

"Chaotic brain activity," Elbert et al., *Electroencephalogr Clin Neurophysiol Suppl*, 1995, vol. 44, pp. 441-449.

"Is the Heart Preadapted to Hypoxia? Evidence from Fractal Dynamics of Heartbeat Interval Fluctuations at High Altitude (5,050 m)," Meyer et al., *Integrated Physiological and Behavioral Science*, Jan.-Mar. 1998, vol. 33, No. 1, pp. 9-40.

"Stability of Heartbeat Interval Distributions in Chronic High Altitude Hypoxia," Meyer et al., *Integrated Physiological and Behavioral Science*, Oct.-Dec. 1998, vol. 33, No. 4, pp. 344-362.

"Event-related dimensional reductions of the primary auditory cortex of he conscious cat are revealed by new techniques for enhancing the non-linear dimensional algorithms", Skinner et al., *International Journal of Psychophysiology*, 1999, pp. 21-35.

"Nonlinear dynamics of heart rate variability during experimental hemorrhage in ketamine-anesthetized rats," Skinner et al., *American J Physiol Heart Circ Physiol*, 2000, 297, pp. 1669-1678.

"The role of the thalamic reticular neurons in alpha- and gamma-oscillations in neocortex: a mechanism for selective perception and stimulus binding," Skinner et al., *Acta Neurobiol. Exp.*, 2000, 60: pp. 123-142.

"Response Cooperativity": A Sign of a Nonlinear Neocortical Mechanism for Stimulus-Binding During Classical Conditioning in the Act, Skinner et al.,Nonlinear Phenomena in Biological and Physical Sciences, Indian National Science Academy, pp. 224-248 (2000).

"Brain Involvement in Cardiovascular Disorders," Skinner, *Behavioral Medicine in Cardiovascular Disorders*, 1988, pp. 229-253.

"The Chaotic Correlation Dimension of the Heartbeat is Reduced by Ischemia," Skinner et al., *Biotech USA, Proceedings of the 6th annual industry conference and exhibition*, Oct. 2-4, 1989, San Francisco, pp. 425-434.

"Chaotic Attractors in a Model of Neocortex: Dimensionalities of Olfactory Bulb Surface Potentials Are Spacially Uniform and Event Related," Skinner et al., *Springer Series in Brain Dynamics 2*, 1989, pp. 158-173.

"Chaos in the Heart: Implications for Clinical Cardiology," Skinner et al., *Bio/Technology*, Nov. 1990, vol. 8, pp. 1018-1024.

"Brain Control of Cardiovascular Dynamics," Skinner, *Event-Related Brain Research*, 1991, pp. 270-283.

"Correlation Dimension of Heartbeat Intervals Is Reduced in Conscious Pigs by Myocardial Ischemia," Skinner et al., *Circulation Research*, vol. 68, No. 4, Apr. 1991, pp. 966-976.

"Neurocardiology Shows that the Central, Not Peripheral, Action of Propranolol Reduces Mortality Following Acute Coronary Occlusion in the Conscious Pig," Skinner, *Integrative Physiological and Behavioral Science*, Apr.-Jun. 1991, vol. 26, No. 2, pp. 85-97.

"Correlation Dimension Changes of the EEG During the Wakefulness-Sleep Cycle," Molner et al., *Acta Biochim. Biophys. Hung.* 26 (1-4), 1991/92, pp. 121-125.

"Application of Chaos Theory to Biology and Medicine," Mitra, *Integrative Physiological and Behavioral Science*, Jan.-Mar. 1992, vol. 27, No. 1, pp. 39-53.

"A reduction in the correlation dimension of heartbeat intervals precedes imminent ventricular fibrillation in human subjects," Skinner et al., *American Heart Journal*, 1993, vol. 125, No. 3, pp. 731-743.

"Neurocardiology Brain Mechanisms Underlying Fatal Cardiac Arrhythmias," Skinner, *Neurocardiology*, vol. 11, No. 2, May 1993, pp. 325-351.

"The Point Correlation Dimension of R-R Intervals Predicts Sudden Cardiac Death Among High-Risk Patients," Vybiral et al., *Computers In Cardiology*, 1993, IEEE Computer Society Press, pp. 257-260.

"Forebrain Regulation of Cardiac Function Spectral and Dimensional Analysis of RR and QT Intervals," Negoescu et al., *Integrative Physiological and Behavioral Science*, Oct.-Dec. 1993, vol. 28, No. 4, pp. 331-342.

"Higher Cerebral Regulation of Cardiovascular and Respiratory Functions," Skinner et al., *Principles and Practice of Sleep Medicine*, Chapter 18, pp. 231-251, 2d Ed. 1993.

"Chaos and Physiology: Deterministic Choas in Excitable Cell Assemblies," Elbert et al., *The American Physiological Society*, vol. 74, No. 1, Jan. 1994, pp. 1-47.

"Neurocardiology: How Stress Produces Fatal Cardiac Arrhythmias," Skinner, 1994, pp. 195-209.

"The Point of Correlation Dimension: Performance with Nonstationary Surrogate Data and Noise," Skinner et al., *Integrative Physiological and Behavioral Science*, Jul.-Sep. 1994, vol. 29, No. 3, pp. 217-234.

"Low-dimensional Chaos in Biological Systems," Skinner, *Bio/Technology*, vol. 12, Jun. 1994, pp. 596-600.

"What Have We Learned and Where Are We Going?," (Postscript), *Integrative Physiological and Behavioral Science*, Jul.-Sep. 1994, vol. 29, No. 3, pp. 234-237.

"The Role of the Central Nervous System in Sudden Cardiac Death: Heartbeat Dynamics in Conscious Pigs during Coronary Occlusion, Psychologic Stress and Intracerebral Propranolol," Skinner, *Integrative Physiological and Behavioral Science*, Oct.-Dec. 1994, vol. 29, No. 4, pp. 355-361.

"Correlation dimension changes accompanying the occurance of the mismatch negativity and the P3 event-related potential component," Molnar et al., *Electroencephalography & Clinical Neurophysiology*, 1995, pp. 118-126.

"Application of Chaos Theory to a Model Biological System: Evidence of Self-Organization in the Intrinsic Cardiac Nervous System," Skinner et al., *Integrative Physiological and Behavioral Science*, Apr.-Jun. 1996, vol. 31, No. 2, pp. 122-146.

"Heart Rate Variability in the Human Transplanted Heart: Nonlinear Dynamics and QT vs RR-QT Alterations during Exercise Suggest a Return of Neurocardiac Regulation in Long-term Recovery," Meyer et al., *Integrative Physiological and Behavioral Science*, Oct.-Dec. 1996, vol. 31, No. 4, pp. 289-305.

"Dynamical Analysis of Heartbeat Interval Time Series After Cardiac Transplantation," Meyer et al. ,Fractals in Biology and Medicine (1997), pp. 139-151.

"Low-Dimensional Chaos in Large Conductance Ca-Activated K-Channel Gating Kinetics," Meyer et al., Fractals in Biology and Medicine (1997), pp. 152-164.

"New Nonlinear Algorithms for Analysis of Heart Rate Variability: Low-Dimensional Chaos Predicts Lethal Arrhythmias," Nonlinear Analysis of Physiological Data, Skinner et al., 1998, pp. 129-166.

"Low-dimensional Chaos in a Simple Biological Model of Neocortex: Implications for Cardiovascular and Cognitive Disorders," Skinner et al., *An International Perspective on Self-regulation and Health*, 1989, pp. 1-29, 1991, pp. 95-117.

Austin AR, Pawson L, Meek S, Webster S, "Abnormalities of heart rate and rhythm in bovine spongiform encephalopathy," *Vet Rec*, 1997, 141(14):352-357.

Braun C, Kowallik P, Freking A, Hadeler D, Kniffki KD, Meesmann M, "Demonstration of nonlinear components in heart rate variability of healthy persons.," *Am J Physiol*, 1998, 275:H1577-H1584.

Kostelich EJ, Swinney HL, "Practical considerations in estimating dimension from time series data," *Physica Scripta*, 1989, 40:436-441.

Marwan N, Wessel N, Meyerfeldt U, Schirdewan A, Kurths J, "Recurrence-plot-based measures of complexity and their application to heart-rate-variability data," *Phys Rev E Stat Nonlin Soft Matter Phys*, 2002, 66:026702.

Skinner JE, "How the head rules the heart,"In: *Life-threatening Arrhythmias During Ischemia and Infarction*, edited by D J Hearse, A S Manning and MJ Janse, Raven Press, New York, 1987, 135-151.

Skinner JE, "Reduction of cardiac vulnerability during REM sleep in the pig," In: *Sleep Disorders, Basic and Clinical Research*, edited by M Chase and ED Weitzman, New York: Spectrum Publications, 1983, 49-63.

Skinner JE, "Regulation of cardiac vulnerability by the cerebral defense system," *J Am Coll Card*, 1985, 5:88B-94B.

Skinner JE, Douglis F, Harper RM, "Higher cerebral regulation of cardiovascular and respiratory functions," *Principles and Practice of Sleep Medicine*, Edited by MH Kryger, T Roth and WC Dement, WB Saunders Co, 1989, Chapter 27, 276-292.

Skinner JE, et al., "Blockade of frontocortical-brain stem pathway prevents ventricular fibrillation of ischemic heart," *Am. J. Physiol.*, 1981, 240: H156-H163.

Skinner JE, et al., "Comparison of linear-stochastic and nonlinear -deterministic algorithms in the analysis of human ECG data to predict risk of arrhythmic death," *Amer J Physiol*, (Submitted, Oct. 2004).

Skinner JE, et al., "Sleep-stage regulation of ventricular arrhythmias in the unanesthetized pig," *Circ. Res.*, 1975, 37: 342-349.

Skinner JE, et al., "Task Force Report on sudden cardiac death and arrhythmias," In: *Circulation, Neurobiology, and Behavior*, edited by OA Smith, RA Galosy and S M Weiss, New York: Elsevier Biomedical Press, 1982, 309-316.

Winfree AT, "Electrical turbulence in three-dimensional heart muscle," *Science*, 1994, 266:1003-1006.

Winfree AT, "Sudden cardiac death: a problem in topology,"*Sci Am*, 1983, 248:144-161.

Winfree AT, "When Time Breaks Down: the three-dimensional dynamics of electrochemical waves and cardiac arrhythmias," 1987, *Princeton U Press*, Princeton NJ, 3-124.

* cited by examiner

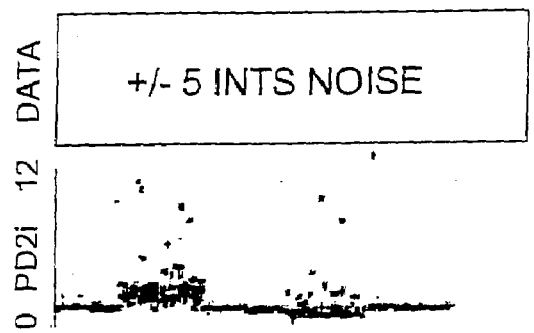
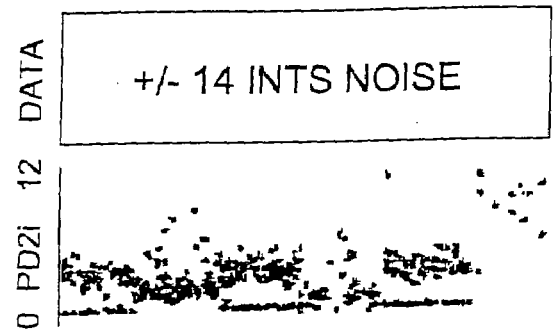
FIG. 2A
FIG. 2B
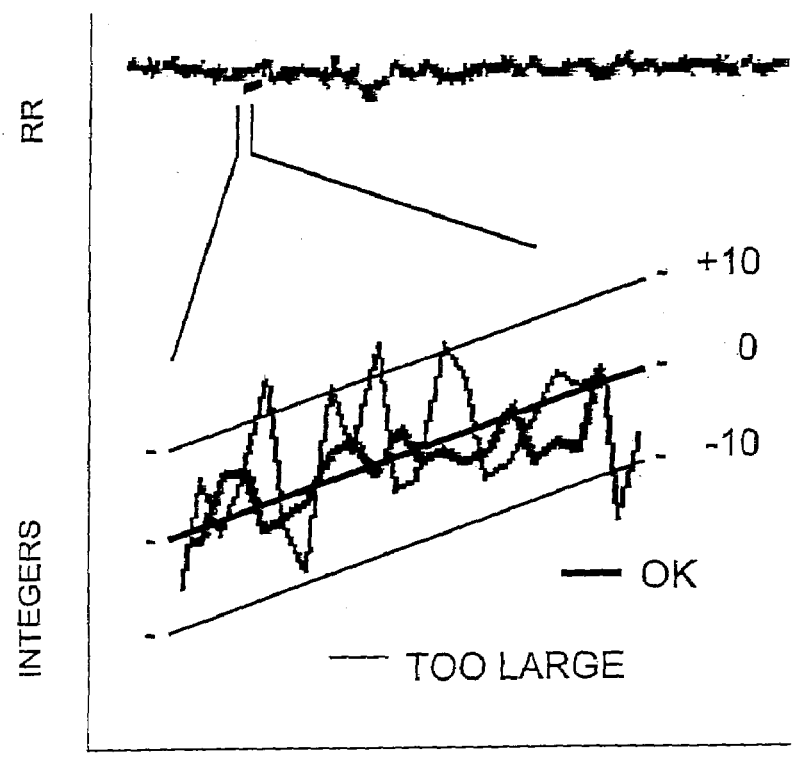
FIG. 3

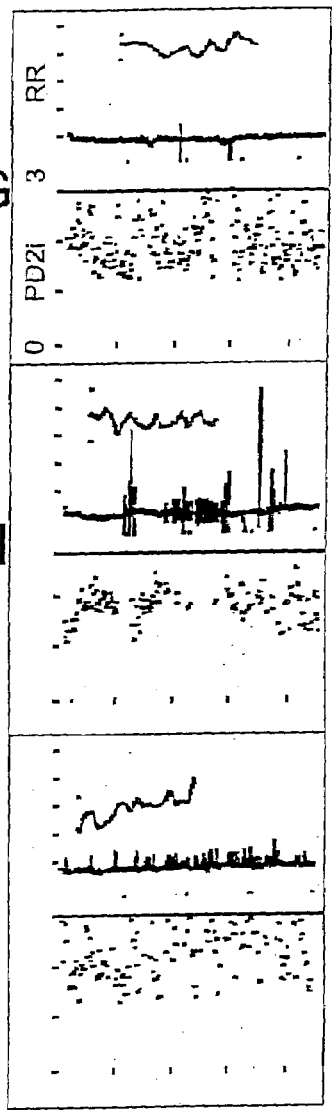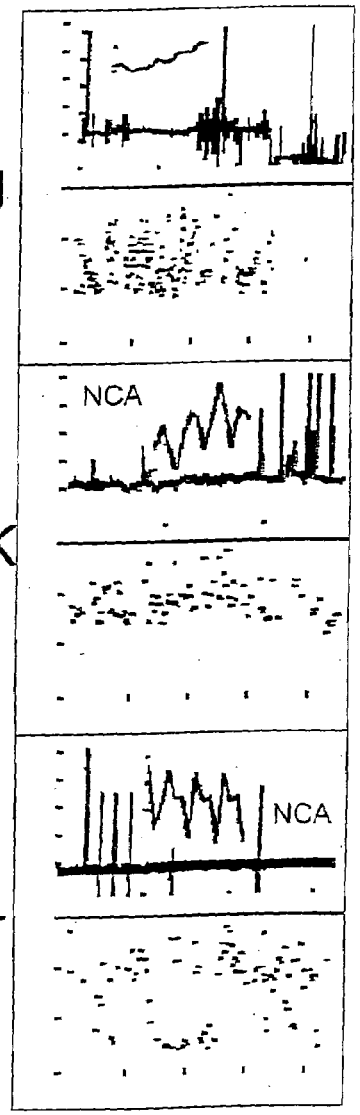
FIG. 4G FIG. 4H FIG. 4I FIG. 4J FIG. 4K FIG. 4L

METHOD AND SYSTEM FOR DETECTING AND/OR PREDICTING CEREBRAL DISORDERS

CROSS-REFERENCE TO RELATED APPLICATIONS

This application is a Continuation-in-part of U.S. Utility Application No. 10/353,849 filed Jan. 29, 2003 now U.S. Pat. No. 7,076,288. In addition, this application claims priority from U.S. Provisional Application No. 60/445,495 filed Feb. 6, 2003. These applications are hereby incorporated by reference.

BACKGROUND

The present invention is directed to a method and system for evaluating biological or physical data. More particularly, the present invention is directed to a system and method for evaluating biological or physical data for detecting and/or predicting cerebral disorders.

The recording of electrophysiological potentials has been available to the field of medicine since the invention of the string galvanometer. Since the 1930's, electrophysiology has been useful in diagnosing cardiac injury and cerebral epilepsy.

The state-of-the-art in modern medicine shows that analysis of R-R intervals observed in the electrocardiogram or of spikes seen in the electroencephalogram can predict future clinical outcomes, such as sudden cardiac death or epileptic seizures. Such analyses and predictions are statistically significant when used to discriminate outcomes between large groups of patients who either do or do not manifest the predicted outcome, but known analytic methods are not very accurate when used for individual patients. This general failure of known analytic measures is attributed to the large numbers of false predictions; i.e., the measures have low statistical sensitivity and specificity in their predictions.

It is usually known that something "pathological" is going on in the biological system under study, but currently available analytic methods are not sensitive and specific enough to permit utility in the individual patient.

The inaccuracy problems prevalent in the art are due to current analytic measures (1) being stochastic (i.e., based on random variation in the data), (2) requiring stationarity (i.e., the system generating the data cannot change during the recording), and (3) being linear (i.e., insensitive to nonlinearities in the data which are referred to in the art as "chaos").

Many theoretical descriptions of dimensions are known, such as "D0" (Hausdorff dimension), "D1" (information dimension), and "D2" (correlation dimension).

D2 enables the estimation of the dimension of a system or its number of degrees of freedom from an evaluation of a sample of data generated. Several investigators have used D2 on biological data. However, it has been shown that the presumption of data stationarity cannot be met.

Another theoretical description, the Pointwise Scaling Dimension or "D2i", has been developed that is less sensitive to the non-stationarities inherent in data from the brain, heart or skeletal muscle. This is perhaps a more useful estimate of dimension for biological data than the D2. However, D2i still has considerable errors of estimation that might be related to data non-stationarities.

A Point Correlation Dimension algorithm (PD2) has been developed that is superior to both the D2 and D2i in detecting changes in dimension in non-stationary data (i.e., data made by linking subepochs from different chaotic generators).

An improved PD2 algorithm, labeled the "PD2i" to emphasize its time-dependency, has been developed. This uses an analytic measure that is deterministic and based on caused variation in the data. The algorithm does not require data stationarity and actually tracks non-stationary changes in the data. Also, the PD2i is sensitive to chaotic as well as non-chaotic, linear data. The PD2i is based on previous analytic measures that are, collectively, the algorithms for estimating the correlation dimension, but it is insensitive to data non-stationarities. Because of this feature, the PD2i can predict clinical outcomes with high sensitivity and specificity that the other measures cannot.

The PD2i algorithm is described in detail in U.S. Pat. No. 5,709,214 and 5,720,294, hereby incorporated by reference. For ease of understanding, a brief description of PD2i and comparison of this measure with others are provided below.

The model for the PD2i is $C(r,n,ref^*,) \sim r^{expD2}$, where $ref^*$ is an acceptable reference point from which to make the various m-dimensional reference vectors, because these will have a scaling region of maximum length PL that meets the linearity (LC) and convergence (CC) criteria. Because each $ref^*$ begins with a new coordinate in each of the m-dimensional reference vectors and because this new coordinate could be of any value, the PD2i's may be independent of each other for statistical purposes.

The PD2i algorithm limits the range of the small log-r values over which linear scaling and convergence are judged by the use of a parameter called Plot Length. The value of this entry determines for each log-log plot, beginning at the small log-r end, the percentage of points over which the linear scaling region is sought.

In non-stationary data, the small log-r values between a fixed reference vector (i-vector) in a subepoch that is, say, a sine wave, when subtracted from multiple j-vectors in, say, a Lorenz subepoch, will not make many small vector-difference lengths, especially at the higher embedding dimensions. That is, there will not be abundant small log-r vector-difference lengths relative to those that would be made if the j-vector for the Lorenz subepoch was instead in a sine wave subepoch. When all of the vector-difference lengths from the non-stationary data are mixed together and rank ordered, only those small log-r values between subepochs that are stationary with respect to the one containing the reference vector will contribute to the scaling region, that is, to the region that will be examined for linearity and convergence. If there is significant contamination of this small log-r region by other non-stationary subepochs, then the linearity or convergence criterion will fail, and that estimate will be rejected from the PD2i mean.

The PD2i algorithm introduced to the art the idea that the smallest initial part of the linear scaling region should be considered if data non-stationarities exist (i.e. as they always do in biological data). This is because when the j-vectors lie in a subepoch of data that is the same species as that the i-vector (reference vector) is in, then and only then will the smallest log-r vectors be made abundantly, that is, in the limit or as data length becomes large. Thus, to avoid contamination in the correlation integral by species of data that are non-stationary with respect to the species the reference vector is in, one skilled in the art must look only at the slopes in the correlation integral that lie just a short distance beyond the "floppy tail".

The "floppy tail" is the very smallest log-r range in which linear scaling does not occur due to the lack of points in this part of the correlation integral resulting from finite data length. Thus, by restricting the PD2i scaling to the smallest part of the log-r range above the "floppy tail," the PD2I algorithm becomes insensitive to data non-stationarities. Note that the D2i always uses the whole linear scaling region, which always will be contaminated if non-stationarities exist in the data.

FIG. 1A shows a plot of log C(r,n,nref*) versus log r. This illustrates a crucial idea behind the PD2i algorithm. It is only the smallest initial part of the linear scaling region that should be considered if data non-stationarities exist. In this case the data were made by concatenating 1200 point data subepochs from a sine wave, Lorenz data, a sine wave, Henon data, a sine wave, and random noise. The reference vector was in the Lorenz subepoch. For the correlation integral where the embedding dimension m=1, the segment for the floppy tail ("FT") is avoided by a linearity criterion of LC=0.30; the linear scaling region for the entire interval (D2i) is determined by plot length PL=1.00, convergence criterion CC=0.40 and minimum scaling MS=10 points. The species specific scaling region where the i- and j-vectors are both in the Lorenz data (PD2i) is set by changing plot length to PL=0.15 or lower. Note that at the higher embedding dimensions (e.g. m=12) after convergence of slope vs embedding dimension has occurred, the slope for the PD2i segment is different from that of D2i. This is because the upper part of the D2i segment (D2i-PD2i) is contaminated by non-stationary i-j vector differences where the j-vector is in a non-stationary species of data with respect to the species the i-vector is in.

This short-distance slope estimate for PD2i is perfectly valid, for any log-log plot of a linear region; it does not matter whether or not one uses all data points or only the initial segment to determine the slope. Thus, by empirically setting Plot Length to a small interval above the "floppy tail" (the latter of which is avoided by setting the linearity criterion, LC), non-stationarities can be tracked in the data with only a small error, an error which is due entirely to finite data length, and not to contamination by non-stationarities.

Thus, by appropriate adjustments in the algorithm to examine only that part of the scaling region just above the "floppy tail", which is determined by, (1) the Linearity Criterion, LC, (2) the Minimum Scaling criterion, MS, and (3) the Plot Length criterion, PL, one skilled in the art can eliminate the sensitivity of the measure to data non-stationarities.

This is the "trick" of how to make the j-vectors come from the same data species that the i-vector is in, and this can be proven empirically by placing a graphics marker on the i- and j-vectors and observing the markers in the correlation integral. This initial part of the scaling region is seen mathematically to be uncontaminated only in the limit, but practically speaking it works very well for finite data. This can be proven computationally with concatenated data. When the PD2i is used on concatenated subepochs of data made by sine-, Lorenz-, Henon-, and other types of known linear and nonlinear data-generators, the short scaling segment will have vector-difference lengths made only by i- and j-vector differences that are stationary with respect to each other; that is, the errors for 1,200-point subepochs are found to be less than 5.0% from their values at the limit, and these errors are due to the finite data length, not scaling contamination.

FIG. 1B illustrates a comparison of the calculation of the degrees of freedom of a data series by two nonlinear algorithms, the Point Correlation Dimension (PD2i) and the Pointwise Scaling Dimension (D2i). Both of these algorithms are time-dependent and are more accurate than the classical D2 algorithm when used on non-stationary data. Most physiological data are nonlinear because of the way the system is organized (the mechanism is nonlinear). The physiological systems are inherently non-stationary because of uncontrolled neural regulations (e.g., suddenly thinking about something "fearful" while sitting quietly generating heartbeat data).

Non-stationary data can be made noise-free by linking separate data series generated by mathematical generators having different statistical properties. Physical generators will always have some low-level noise. The data shown in FIG. 1B (DATA) were made of sub-epochs of sine (S), Lorenz (L), Henon (H) and random (R) mathematical generators. The data series is non-stationary by definition, as each sub-epoch (S, L, H, R) has different stochastic properties, i.e., different standard deviations, but similar mean values. The PD2i and D2i results calculated for the data are seen in the two traces below it and are very different. The D2i algorithm is the closest comparison algorithm to PD2i, but it does not restrict the small log-r scaling region in the correlation integral, as does the PD2i. This scaling restriction is what makes the PD2i work well on non-stationary data.

The PD2i results shown in FIG. 1B, using default parameters, (LC=0.3, CC=0.4, Tau=1, PL=0.15), are for 1,200 data-point sub-epochs. Each sub-epoch PD2i mean is within 4% of that known value of D2 calculated for each data type alone (using long data lengths). The known D2 values for S, L, H, and R data are, respectively, 1.00, 2.06, 1.26, and infinity. Looking at the D2i values, one sees quite different results (i.e., spurious results). Note that the D2i is the closest algorithm to PD2i, because it too is time-dependent. However, D2i it requires data stationarity, as does the D2 value itself. For stationary data, D2=D2i=PD2i. Only the PD2i tracks the correct number of degrees of freedom for non-stationary data. The single value of D2 calculated for the same non-stationary data is approximated by the mean of the D2i values shown.

For analysis by the PD2i, an electrophysiological signal is amplified (gain of 1,000) and digitized (1,000 Hz). The digitized signal may be further reduced (e.g. conversion of ECG data to RR interval data) prior to processing. Analysis of RR-interval data has been repeatedly found to enable risk-prediction between large groups of subjects with different pathological outcomes (e.g. ventricular fibrillation "VF" or ventricular tachycardia "VT"). It has been shown that, using sampled RR data from high risk patients, PD2i could discriminate those that later went into VF from those that did not.

For RR-interval data made from a digital ECG that is acquired with the best low-noise preamps and fast 1,000-Hz digitizers, there is still a low-level of noise that can cause problems for nonlinear algorithms. The algorithm used to make the RR-intervals can also lead to increased noise. The most accurate of all RR-interval detectors uses a 3-point running "convexity operator." For example, 3 points in a running window that goes through the entire data can be adjusted to maximize its output when it exactly straddles an R-wave peak; point 1 is on the pre R-wave baseline, point 2 is atop the R-wave, point 3 is again on the baseline. The location of point 2 in the data stream correctly identifies each R-wave peak as the window goes through the data. This algorithm will produce considerably more noise-free RR data than an algorithm which measures the point in time when an R-wave goes above a certain level or is detected when the dV/dt of each R-wave is maximum.

The best algorithmically calculated RR-intervals still will have a low-level of noise that is observed to be approximately +/−5 integers, peak-to-peak. This 10 integer range is out of 1000 integers for an average R-wave peak (i.e., 1% noise). With poor electrode preparation, strong ambient electromagnetic fields, the use of moderately noisy preamps, or the use of lower digitizing rates, the low-level noise can easily increase. For example, at a gain where 1 integer=1 msec (i.e., a gain of 25% of a full-scale 12-bit digitizer), this best noise level of 1% can easily double or triple, if the user is not careful with the data acquisition. This increase in noise often happens in a busy clinical setting, and thus post-acquisition consideration of the noise level must be made.

There is thus a need for an improved analytic measure that takes noise into consideration. There is also a need for such a measure in the medical field, e.g., to detect biological anomalies, such as cerebral disorders.

SUMMARY

The objects, advantages and features of the present invention will become more apparent when reference is made to the following description taken in conjunction with the accompanying drawings.

According to exemplary embodiments, cerebral disorders are detected and/or predicted by analyzing input biological or physical data using a data processing routine. The data processing routine includes a set of application parameters associated with biological data correlating with the biological anomalies. The data processing routine uses an algorithm to produce a data series, e.g., a PD2i data series, which is used to detect or predict the onset of the biological anomalies.

According to one aspect of the invention, to reduce noise in the data series, the slope is set to a predetermined number, e.g., zero, if it is less than a predetermined value, e.g., 0.5.

According to another aspect, a noise interval within the data series is determined and, if the noise interval is within a predetermined range, the data series is divided by another predetermined number, e.g., 2, and new values are produced for the data series.

According to exemplary embodiments, reducing the noise in the data series improves detection/prediction of the onset of cerebral disorders, such as human prion diseases (Jacob-Creutzfeld Disease) and the various dementias (cardiovascular, traumatic, genetic), including Alzheimer's disease. The methods of the present invention can also be utilized to detect and predict the onset of bovine spongioform encephalitis, sheep scrapie and elk wasting disease.

BRIEF DESCRIPTION OF THE DRAWINGS

FIGS. 2A and 2B illustrate performance of PD2i when low-level noise is added to the non-stationary data;

FIG. 3 illustrates examination of low-level noise in two sets of RR-intervals made from two digital ECG's;

FIGS. 4G-4L illustrate low level noise in the RR-intervals of arrhythmic death patients;

DETAILED DESCRIPTION

According to an exemplary embodiment, a technique has been developed to eliminate the contribution of low-level noise to nonlinear analytic measures, such as PD2i.

Figure 1A:
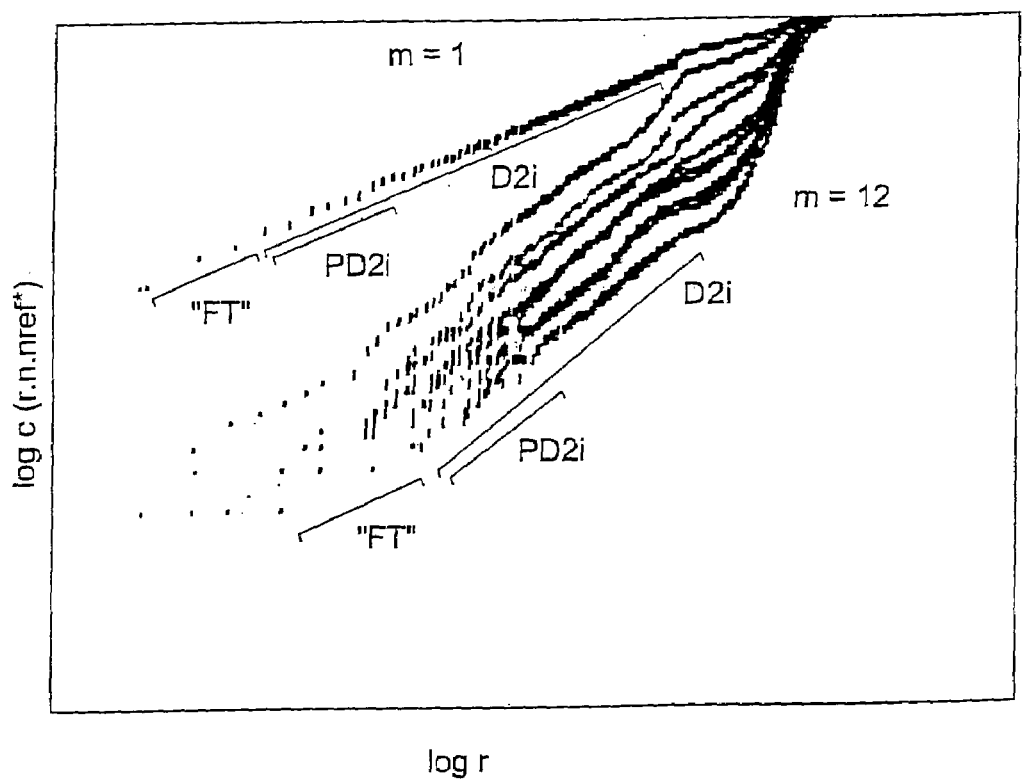
FIG. 1A illustrates a plot of log C(r,n,nref*) versus log r for the conventional PD2i algorithm.
Figure 1B:
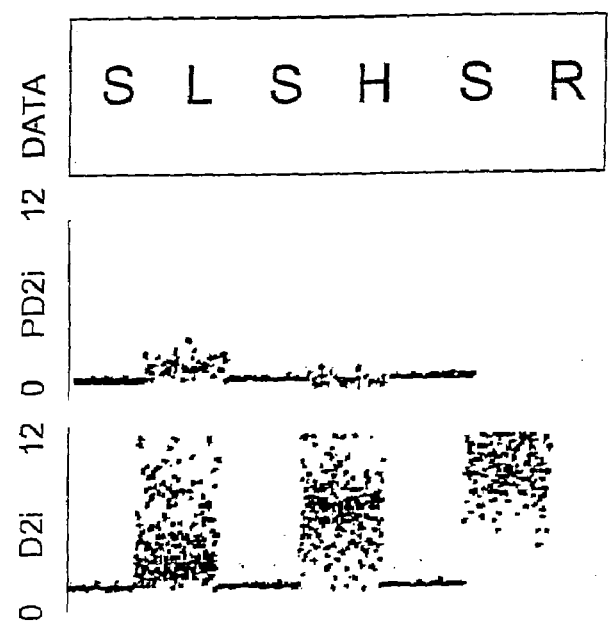
FIG. 1B illustrates a plot showing calculation of degree of freedom (dimensions) by two time-dependent algorithms when applied to noise-free non-stationary data.
Figure 4A:
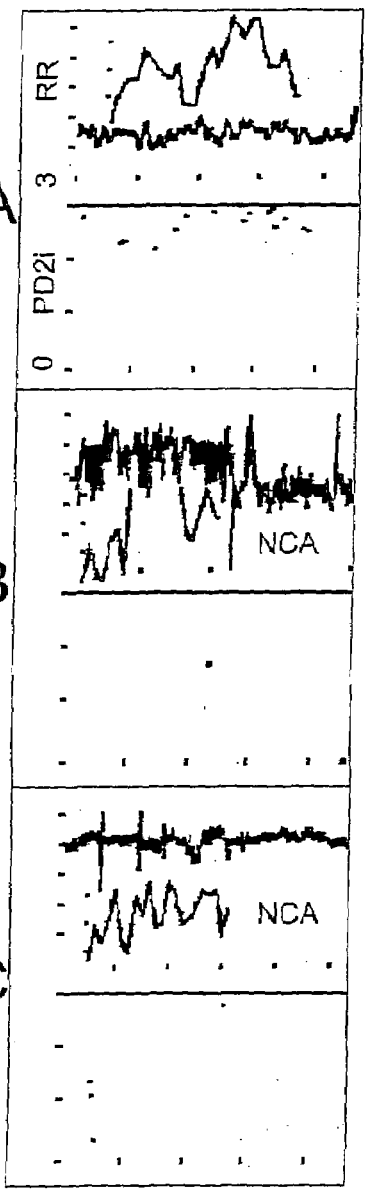
FIGS. 4A-4F illustrate low level noise (insets) in the RR-intervals of control patients with acute myocardial infarctions.
Figure 4B:
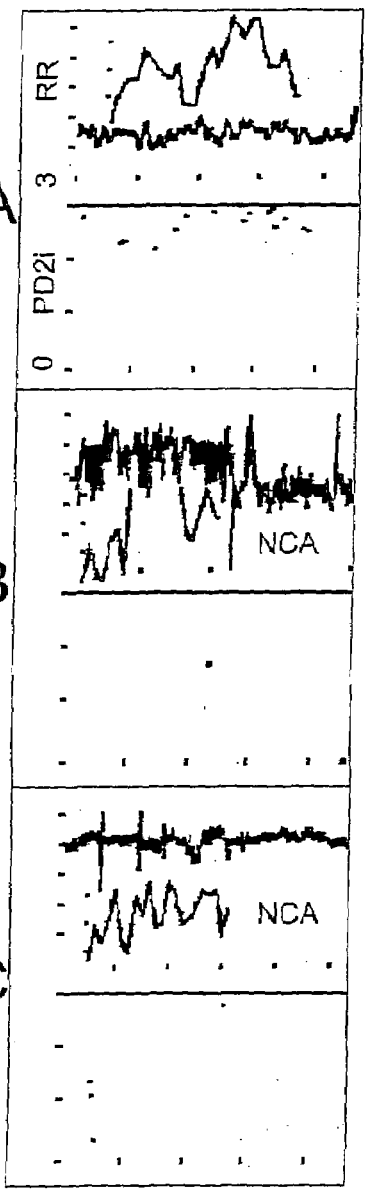
Figure 4C:
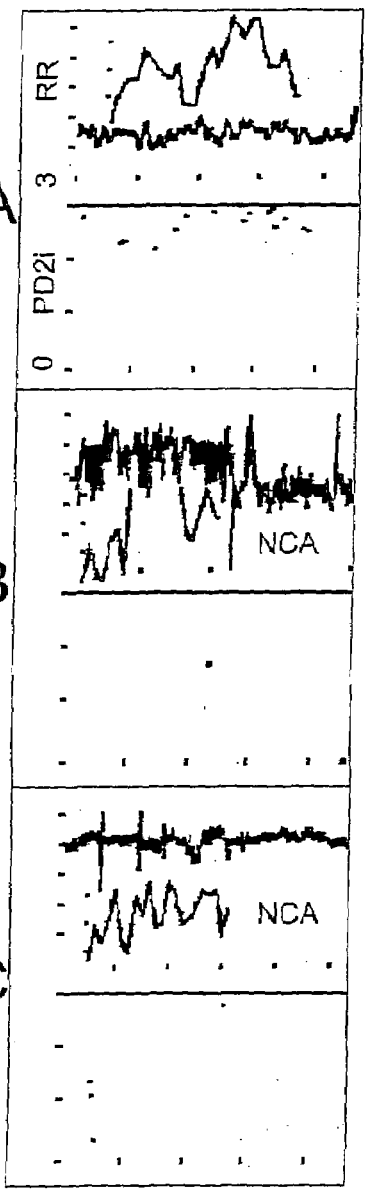
Figure 4D:
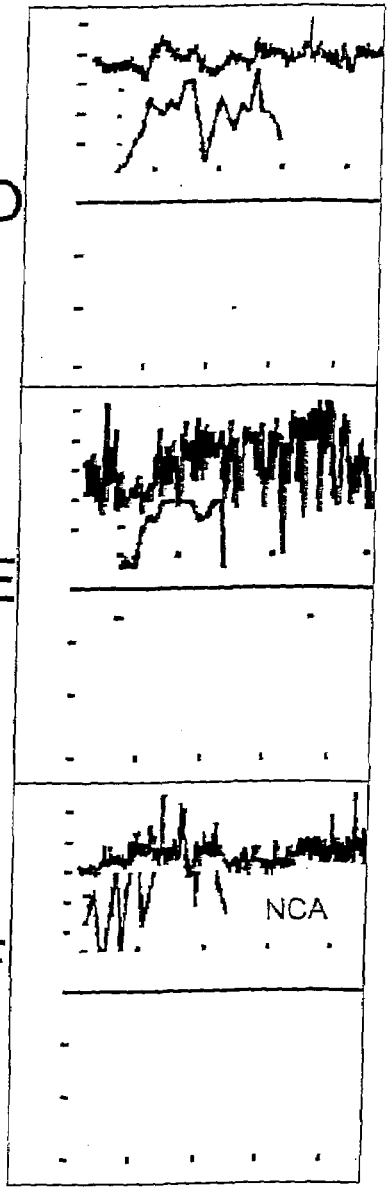
Figure 4E:
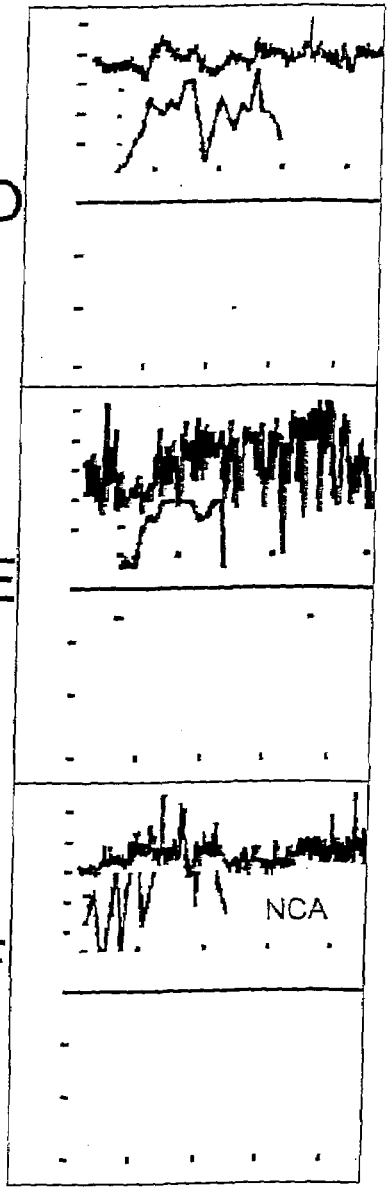
Figure 4F:
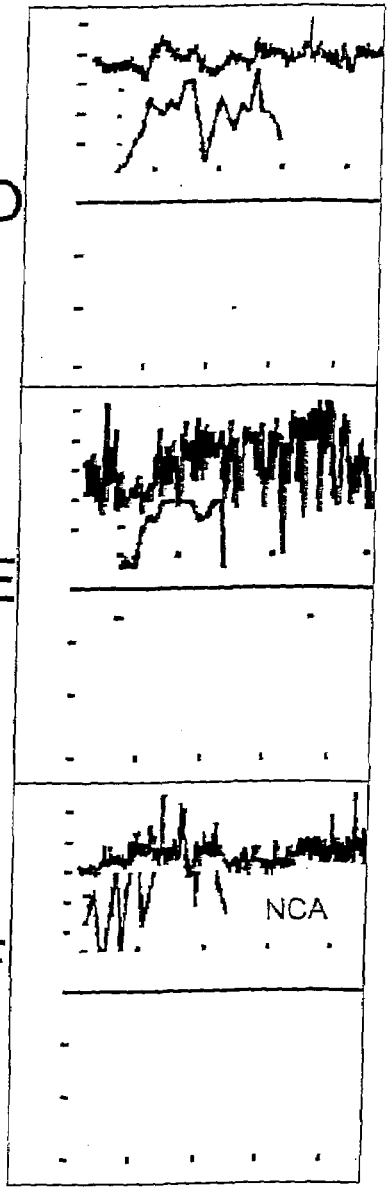

To see why the noise is important, reference is made to FIGS. 2A and 2B. In FIGS. 2A and 2B, the data are the same S, L, H, and R data as described with reference to FIG. 1B. By definition, this data does not have any noise, as it is made by mathematical generators.

In FIG. 2A, $\forall 5$ integers of low-level noise have been added to the non-stationary data series. The mean values of PD2i for each sub-epoch have not changed significantly, although there are a few large values out of the 1200 data points in each of the sub-epochs.

Adding noise of $\forall 14$ integers, however, now results in spurious PD2i values, the means of which are all approximately the same, as shown in FIG. 2B.

According to exemplary embodiments, the NCA (noise consideration algorithm) examines the low level noise at high magnification (e.g., y axis is 40 integers full scale, x-axis is 20 heartbeats full scale) and determines whether or not the noise is outside a predetermined range, for example, whether the dynamic range of the noise is greater than $\forall 5$ integers. If it is, then the data series is divided by a number that brings the noise back within the range of $\forall 5$ integers. In this example, the data series may be divided by 2, as only the low-level bit of the 12 bit integer data contains the noise.

Since the linear scaling region of the correlation integral, calculated at embedding dimensions less than m=12, will have slopes less than 0.5 when made from low-level noise (e.g., with a dynamic range of $\forall 5$ integers), it is impossible to distinguish between low-level noise and true small slope data. Conveniently, since slopes less than 0.5 are rarely encountered in biological data, the algorithmic setting of any slopes of 0.5 or less (observed in the correlation integral) to zero will eliminate the detection of these small natural slopes, and it will also eliminate the contribution of low-level noise to the PD2i values. It is this "algorithmic phenomenon" that explains the empirical data and accounts for the lack of effect of noise within the interval between −5 and 5 when added to noise-free data (FIG. 2A). Noise of slightly larger amplitude, however, will show the noise-effects expected to occur with nonlinear algorithms (e.g., FIG. 2B).

Based on application to physiological data, it is now understood that the low-level noise must always be considered and somehow kept within a predetermined range, such as between $\forall 5$ integers, or any other range that is a relevant one based on the empirical data. This consideration will prevent spurious increases of PD2i for low-dimensional data (i.e., data with few degrees of freedom) as illustrated by FIG. 2B. The proof of the concept lies in its simple explanation ("algorithmic phenomenon"), but perhaps even more convincing are the empirical data that support the use of an NCA. These data will now be presented.

The upper portion of FIG. 3 shows clinical RR-interval data from a patient who died of arrhythmic death (AD). A small segment of 20 heartbeats of the RR-interval data is magnified and shown at the bottom portion of FIG. 3. The linear regression represents the slow variation in the signal in the segment of data, while the up-and-down sawtooth variations represent the noise. Both ECG's and RR's appeared similar, but low-level observations of the data (20 heartbeats, 40-integer y-axis) revealed that one had data variation ranging between ±5 integers (OK) and the other between ±10 integers (too large). the larger-amplitude segment ("too large") is not identified and corrected, then the PD2i values would be spuriously larger, as in FIG. 2B. A consequence of such spuriously larger PD2i values is that a PD2i-based test might make the wrong clinical prediction about the vulnerability of the patient's heart to lethal arrhythmogenesis.

According to exemplary embodiments, a larger-amplitude segment like that shown in FIG. 3 (too large) can be identified and corrected using the noise consideration algorithm (NCA).

Tables 1-4 show clinical data obtained as part of a study supporting the NCA concept. The goal of the study presented in Tables 1-4 was to predict the occurrence of arrhythmic death (AD) from a PD2i-test performed on the digital ECG of each patient. In a study of 320 patients exhibiting chest pain in the Emergency Room who were determined to be at high cardiac risk with the Harvard Medical School protocol, approximately one out of 3 patients needed application of the NCA to provide meaningful data. If the NCA had not been developed and applied, then the data obtained from these patients would have been meaningless in those cases where the low-level noise was too large.

Table 1A shows the contingency table of predictive AD outcomes (i.e., true positive, true negative, false positive, false negative) and the Relative Risk statistic (Rel) for the data set analyzed with several nonlinear deterministic algorithms (PD2i, DFA, 1/f-Slope, ApEn). Table 1B shows the contingency table of predictive AD outcomes and Rel for the data set analyzed with the more usual linear stochastic algorithms (SDNN, meanNN, LF/HF, LF(ln)).

Tables 1A and 1B show comparison of HRV algorithms in 320 high-risk patients (N) presenting chest pain in the Emergency Department and having assessed risk of acute-MI>7%. All subjects had ECGs recorded and 12-month follow-up completed. The defined arrhythmic death outcomes are expressed as true or false predictions (T or F) by positive or negative HRV tests (P or N). Abbreviations in the tables are expressed as follows: SEN=sensitivity (%); SPE=specificity (%); REL=relative risk statistic; SUR=surrogate-rejection; OUT=outlier-rejection (>3 SD's); AF=atrial-fib rejection.

Nonlinear Deterministic Algorithms:

TABLE 1A

| PD2i ≤ 1.4 | PD2i > 1.4 | DFAOUT | DFA IN | 1/fS ≤ −1.07 | 1/fS > −1.07 | ApEn ≤ 1 | ApEn > 1 |
|---|---|---|---|---|---|---|---|
| TP = 19 | TN = 140 | TP = 6 | TN = 52 | TP = 6 | TN = 158 | TP = 4 | TN = 166 |
| FP = 96 | FN = 1[#] | FP = 227 | FN = 75 | FP = 14 | FN = 61 | FP = 61 | FN = 16 |
| SEN = 95** | SUR = 65 | SEN = 30 | SUR = 15 | SEN = 30 | SUR = 65 | SEN = 20 | SUR = 65 |
| SPE = 59** | OUT = 0 | SPE = 19 | OUT = 6 | SPE = 68 | OUT = 2 | SPE = 73 | OUT = 8 |
| REL >> 23** | N = 320 | REL = 0.12 | N = 320 | REL = 0.91 | N = 320 | REL = 0.80 | N = 320 |

Linear Stochastic Algorithms:

TABLE 1B

| SDNN ≤ 65 | SDNN > 65 | MNN ≤ 750 | MNN > 750 | LF/HF ≤ 1.6 | LF/HF > 1.6 | LF(ln) ≤ 5.5 | LF(ln) > 5.5 |
|---|---|---|---|---|---|---|---|
| TP = 19 | TN = 59 | TP = 19 | TN = 163 | TP = 7 | TN = 196 | TP = 19 | TN = 96 |
| FP = 202 | FN = 6 | FP = 98 | FN = 6 | FP = 63 | FN = 18 | FP = 163 | FN = 6 |
| SEN = 76 | AF = 29 | SEN = 76 | AF = 29 | SEN = 28 | AF = 29 | SEN = 76 | AF = 29 |
| SPE = 23 | OUT = 5 | SPE = 62 | OUT = 5 | SPE = 76 | OUT = 7 | SPE = 37 | OUT = 7 |
| REL = 0.93 | N = 320 | REL = 4.57* | N = 320 | REL = 1.19 | N = 320 | REL = 1.78 | N = 320 |

**$p \leq 0.001$; Binomial Probability Test; with multiple-test alpha-protection (alpha level required is 8-fold smaller); expansion of $(P + Q)^n \times$ 8-fold protection implies p = 0.00016, which is $p \leq 0.001$; also $p \leq 0.001$ by Fisher's Exact Test for row vs column associations in a 2 × 2 contingency table; all others are not significant by Binomial Probability Test.
*$p \leq 0.001$ Fisher's Exact Test only; i.e., not significant by Binomial Probability Test.
PD2i = Point Correlation Dimension (positive if minimum PD2i ≤ 1.4 dimensions, with a systematic low-dimensional excursion of more than 12 PD2i values); cases of randomized-phase surrogate rejections (SUR) were identical to the cases of $F_N \leq 33\%$.
DFA-OUT = Detrended Fluctuation Analysis ($\alpha_1$ [short-term] is positive, if outside normal range of 0.85 to 1.15); randomized-sequence surrogate rejections (SUR).
1/fS = 1/f Slope (positive, if ≤−1.075 for slope of log[microvolts$^2$/Hz] vs log [Hz] integrated over 0.04 Hz to 0.4 Hz)
ApEn = Approximate Entropy (positive with cut-point ≤1.0 units, slope distance).
SDNN = Standard deviation of normal beats (positive, if ≤65 msec; for positive, if ≤50 msec, TP = 17).
MNN = Mean of normal RR-intervals (positive, if ≤750 msec).
LF/HF = Low frequency power (0.04 to 0.15 Hz)/high frequency power (0.15 to 0.4 Hz) (positive, ≤1.6).
LF(ln) = Low frequency power (0.04 to 0.15 Hz), normalized by natural logarithm (positive, ≤5.5).
This single AD patient died at 79 days and may not be a true FN; the digital ECG was recorded prior to two normal clinical ECGs, followed by a third positive one (i.e., the patient could be classified as an "evolving acute MI" who may have been TN at the time the ECG was recorded).

As can be seen from the data presented in Tables 1A and 1B, only the PD2i algorithm had statistically significant Sensitivity, Specificity, and Relative Risk statistics in this Emergency Room cohort.

Table 2 shows the Relative Risk statistic for various sub-groups of the high-risk cardiac patients. It is clear from the data presented in Table 2 that the PD2i performs best in all of them.

Table 2 shows the relative Risk for algorithmic prediction of arrhythmic death in 320 high-risk cardiac patients in the Emergency Room.

TABLE 2

|  | AMI | Non-AMI | post-MI | non-post-MI |
|---|---|---|---|---|
| PD2i | 7.39** | >12.17** | >4.51* | >16.85** |
| DFA | 0.70 | 0.44 | 0.63 | 0.48 |
| 1/f Slope | 1.67 | 0.56 | 0.87 | 0.90 |
| ApEn | 0.50 | 1.44 | 0.00 | 0.72 |
| SDNN | 0.68 | 1.75 | 0.83 | 1.34 |
| MNN | 1.94 | >20.82** | 3.00 | 3.61* |
| LF/HF | 1.08 | 0.66 | 2.52 | 0.61 |
| LF(ln) | 1.08 | >5.13* | 0.73 | 2.09 |

**$p \leq 0.001$,
*$p \leq 0.05$,
Fisher Exact Test for row vs column association in 2 × 2 contingency table; the > sign means that RR went to infinity because FN = 0; the value shown used FN = 1. Relative Risk = True Positive/False Negative × [True Negative + False Negative/True Positive + False Positive].

Table 3 shows performance of PD2i in the prediction of arrhythmic death in 320 high-risk cardiac patents in the Emergency Room, with and without the use of the NCA on the RR-interval data.

TABLE 3

Table 3 illustrates how the use or non-use of the NCA can change the study

| NCA USED | | NCA NOT USED | |
|---|---|---|---|
| PD2i ≤ 1.4 | PD2i > 1.4 | PD2i ≤ 1.4 | PD2i > 1.4 |
| TP = 19 | TN = 140 | TP = 12 | TN = 140 |
| FP = 96 | FN = 1# | FP = 96 | FN = 8 |
| REL >> 23** | N = 320 | REL = 1.8# | N = 320 |

**$p < 0.001$
Not statistically significant outcome for the Relative Risk statistic. Without the consideration of the noise, the PD2i would not have had such remarkable predictive performance, and none of the other algorithms would have worked very well either.

Table 4 illustrates another PD2i measurement criterion that also works well in predicting AD. Table 4 shows the percentage of all PD2i values between 3 and 0 degrees of freedom (dimensions) for 16 arrhythmic death patients, each of whom died within 180 days of their ECG recording, and their matched controls, each of whom had a documented acute myocardial infarction, but did not die within 1-year of follow-up. The means of the two groups were highly statistically significant (P<0.0000001, t-test).

TABLE 4

| Arrhythmic Death (within 180 days) | | Matched Controls (AMI, no AD 1-yr) | |
|---|---|---|---|
| Patient ID | 3 < % PD2i > 0 | Patient ID | 3 < % PD2i > 0 |
| Bn032 | 95 | Ct024-n | 13 |
| Bn078 | 90 | Gr077-n | 7 |
| Bn100 | 90 | Bn126 | 0 |
| Bn090 | 90 | Bn157 | 0 |
| Bn113 | 70 | Bn138 | 1 |
| Bn137-n | 90 | Bn160 | 0 |
| Bn159 | 98 | Bn167 | *3 |
| Bn141-n | 97 | Ct001 | 0 |
| Bn162 | 80 | B216 | 0 |
| Bn215-n | 55 | C002 | 5 |
| Gr012 | 98 | Bn220 | 1 |
| Bn226-n | 95 | Ct005 | 6 |
| Gr064 | 99 | Ct008-n | 0 |
| B227 | 95 | Ct022-n | 0 |
| Gr076 | 99 | Ct009 | 1 |
| Gr056-n | 65 | Gr047 | 5 |
| Gr107 | 40 | C021 | 0 |
| Gr111 | 90 | Gr090 | 0 |
| Mean ± SD | 83 ± 20** | Mean ± SD | 2.3 ± 3.6** |

*These values were due to excessive ectopic beats that produced some scaling in the 3 to 0 range.
**$P < 0.000001$, t-test; all AD subjects met PD2i < 1.4 LDE and 0 < PD2i > 3.0 criteria; Sensitivity = 100%, Specificity = 100%

As can be seen from Table 4, in the high-risk ER patients who do not die (negative-test) the majority of their PD2i's are above 3 dimensions (degrees of freedom). In those patients who do die (positive-test) the majority of their PD2i's are below 3 dimensions. This % PD2i<3 criterion completely separated the AD patients from their matched controls who had acute myocardial infarctions, but who did not die of AD (sensitivity=100%; specificity=100%). These results too are completely dependent upon the use of the NCA to keep the distributions from overlapping and the Sensitivity and Specificity at 100%. Those subjects in which the noise-bit was removed, that is, because the low-level noise in their RR-intervals was too high, are indicated by –n at the end of the file name.

PD2i Criteria for Predicting Arrhythmic Death

Each of the above Tables 1-4 was based on the observation of a low-dimensional excursion (LDE) to or below a PD2i of 1.4. That is, PD2i<1.4 was the criterion for prediction of AD. There were no false negative (FN) predictions using this criterion. The FN case is anathema to medicine, as the patient is told, "you are OK," but then he or she goes home to die of AD within a few days or weeks. False positive cases are expected in great numbers, as the cohort is a high-risk one having patients with acute myocardial infarctions, monomorphic ectopic foci, and other high-risk diagnoses. These positive-test patients are certainly at risk, and should be hospitalized, but they will not die, perhaps because of the drugs or surgical interventions that are applied in the hospital. In other words, the FP classification is not anathema to medicine. What is significant about the application of the PD2i to these ER patients is, 1) all AD's occurred in positive-test patients, and 2) 51% of the negative-test patients could be safely discharged from hospital, as none died within the year of follow-up. All of these clinical results are meaningful, but are completely dependent upon the use of the NCA to keep the Sensitivity and Specificity at 100% and the Relative Risk high.

FIGS. 4A-4L illustrate the PD2i<1.4 LED's and the % PD2i<3 criteria, both of which would have been changed significantly had the NCA not been used in some cases (NCA). Although they are related to one another, the use of both criteria in NCA examined data is probably the best and most universal way to predict AD among high-risk cardiac patients. This combination keeps statistical Sensitivity and Specificity at 100%, as seen for the AD patients and their acute MI controls (Table 4; FIGS. 4A-4L).

FIGS. 4A-4F illustrate low-level noise in the RR intervals of 6 acute myocardial infarction (acute MI) control patients, and FIGS. 4G-L illustrate low-level noise in the RR intervals of 6 arrhythmic death (AD) patients.

The long segment in each panel represents all of the RR-intervals in the 15 minute ECG. The short segment displays the low-level noise traces from a small 20 beat segment at a higher gain. Thus, in each panel, the noise is superimposed upon larger dynamic activity. All gains are the same for all subjects (long RR trace=500 to 1000 integers; short RR trace=0 to 40 integers).

Those subjects with a noise range judged to be larger than $\forall 5$ integers (1 msec=1 integer) had the noise consideration algorithm (NCA) performed before the PD2i was calculated. Thus, for example, the NCA was applied for the control subjects represented in FIGS. 4B, 4C, and 4F and for the AD subjects represented in FIGS. 4K and 4L.

The PD2i values corresponding to each RRi are displayed on a scale of 0 to 3 dimensions (degrees of freedom). For the AD subjects, as represented in FIGS. 4G-4L, there are many PD2i values less than 3.0. Table 4 shows this to be a mean of 83% of PD2i's below 3.0 for all subjects.

The predictability outcomes for the clinical data would not have been statistically significant without considering the noise content of the data. The NCA actually used in all of the above applications involved, 1) observing whether or not the dynamic range of the noise was outside a 10 integer interval, and then, if it was, 2) reducing the amplitude of the RR's sufficiently to get rid of the excess noise. The NCA was required in approximately ⅓ of the subjects. Rather than multiplying each data point by a value that would just reduce the dynamic range of the noise to under 10-integers, the multiplier was 0.5 (i.e., it removed a whole bit of the 12-bit data).

All applications of NCA were done blinded to the data outcome (arrhythmic death was determined only after PD2i analyses with NCA were completed). This procedure excludes the possibility for experimenter bias and is a required design for statistical analyses.

According to an exemplary embodiment, the noise consideration algorithm as described above may be implemented in software. Determination of the noise interval may be made visually, based on data displayed, e.g., on a computer monitor. The data may be displayed at a fixed magnification, e.g., $\forall 40$ integers full-scale centered around the mean of the segment displayed. If the values are outside the ±5 integer range, the user may decide to divide the data series by a predetermined value, or the division may occur automatically.

Figure 5A:
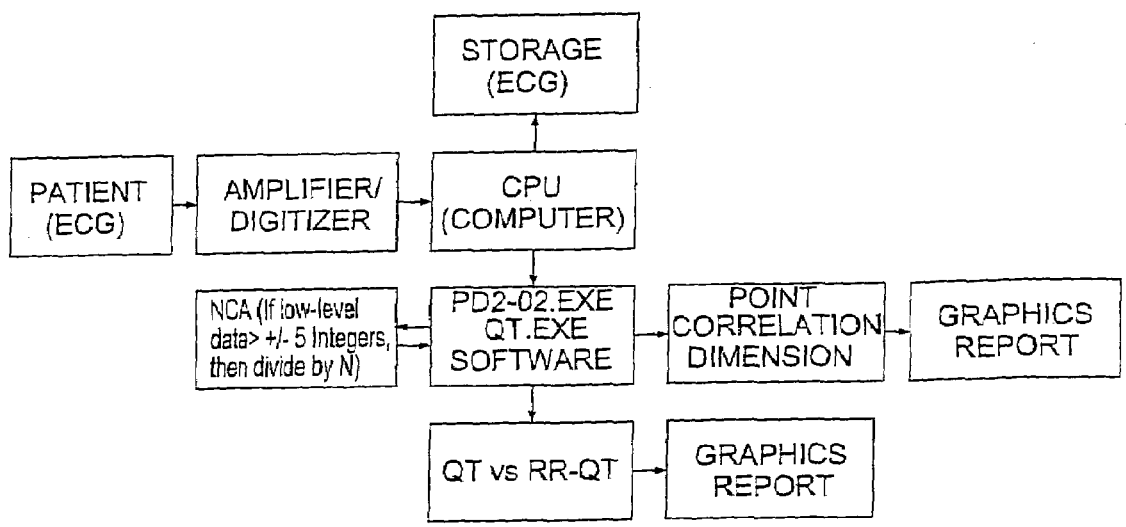
FIG. 5A illustrates an exemplary flow diagram for the logic of the NCA applied to ECG data in cardiology.

FIG. 5A illustrates an exemplary flow diagram for the logic of the NCA applied to ECG data. According to an exemplary embodiment, ECG from the subject is collected by a conventional amplifier, digitized, and then given as input to a computer for analysis. First, RR and QT intervals are made from the ECG data; then they are analyzed by the PD2i software (PD2-02.EXE) and QTvsRR-QT software (QT.EXE).

According to exemplary embodiments, the NCA is applied at two points, e.g., as part of the execution of the PD2i and QT vs RR-QT software and after execution of the PD2i and QT vs RR-QT software. For example, the NCA may be applied during execution of the PD2i and QT vs RR-QT software so that the slope of log $c(n, r, nref^*)$ vs. log r is set to zero if the slope is <than 0.5 and > than zero. Also, the NCA may be applied after execution of the PD2i and QT vs RR-QT software to divide the PD2i data series by a predetermined integer if the low-level noise is outside a predetermined interval, e.g., outside the interval between −5 and 5. If such division occurs, the PD2i calculation is repeated for the divided data by executing the PD2i and QT vs RR-QT software again.

After execution of the PD2i and QT vs RR-QT software is completed, the Point Correlation Dimension is then calculated as a function of time and displayed. The QT vs RR-QT plot is also made and displayed. Graphics Reports are then made for assessing risk. The digitized ECG may be offloaded for storage.

The descriptions above relate largely to improving the detection/prediction of detecting deterministic low-dimensional excursions in non-stationary heartbeat intervals made from ECG data as a harbinger of fatal cardiac arrhythmias. The descriptions above also relate to improving the detection of dynamics of QT vs RR-QT jointly-plotted heartbeat subintervals, in a previously observed exclusion area, as harbingers of fatal cardiac dynamical arrhythmias. It will be appreciated, however, that the invention is also applicable to improving the detection/predication of other biological anomalies using, e.g., electroencephalographic (EEG) data. For example, the NCA may be applicable to improve the detection of persistent alterations in the deterministic dimensional reconstructions made from the non-stationary EEG data as a measure of altered cognitive state. The NCA may also be applicable to improve detection of an enlarged variance in the deterministic dimensional variations in EEG potentials as a harbinger of early paroxysmal epileptic activity.

Figure 5B:
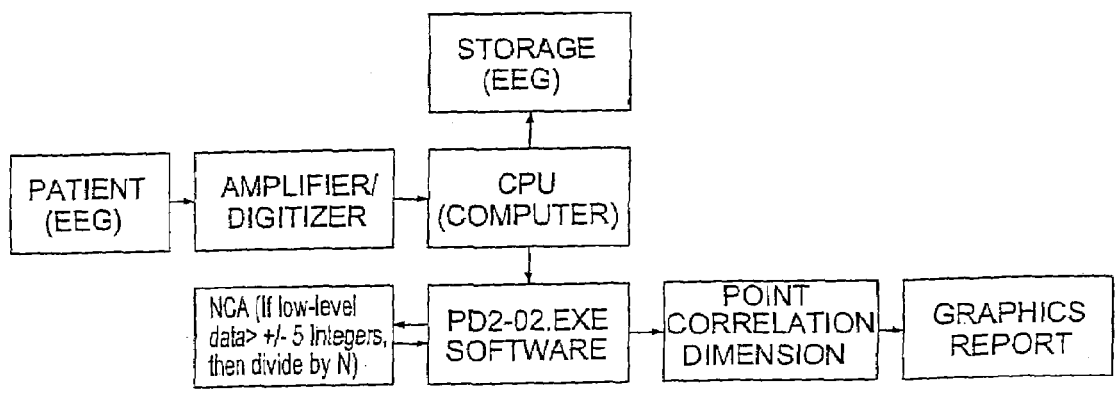
FIG. 5B illustrates an exemplary flow diagram for the logic of the NCA applied to EEG data and related concepts in neurophysiology.

FIG. 5B shows an exemplary implementation of the NCA algorithm for an epilepsy patient or normal subject undergoing neural analysis. EEG data from the subject is made by a conventional amplifier, digitized, and then given as input to a computer for analysis. The PD2i.exe software (PD2-02.exe) is then executed, setting the slope to, e.g., zero as necessary. Next, if the low-level noise is outside a predetermined interval, the PD2i data series is divided by a predetermined integer and the PD2i calculation is repeated for the divided data by executing the PD2i and QT vs RR-QT software again.

The Point Correlation Dimension is then plotted, and a Graphics Report is then made for assessing location of epileptic focii and/or alteration of cognitive state.

The NCA may be implemented on, e.g., a microcomputer. Although shown as separate elements, one or all of the elements shown in FIG. 5A and FIG. 5B may be implemented in the CPU.

Although the focus of the description above has been mainly on the assessment of ECG data and EEG data, it will be appreciated that other similar applications of the invention are possible. The source of the electrophysiological signal may be different, and the structure of the graphics report(s) may be specific to the medical and/or physiological objectives. All analyses may use the PD2i algorithm and the NCA in some software form and may be accompanied by other confirmatory analyses.

The present invention also provides a method of detecting or predicting the onset of a cerebral disorder, comprising the steps of: analyzing input biological or physical data using a data processing routine including a set of application parameters associated with biological data correlating with the cerebral disorder to produce a data series, determining whether a slope of the data series is smaller than a predetermined value; if the slope is less than a predetermined value, setting the slope to a predetermined number; and using the data series to detect or predict the onset of the cerebral disorder.

Figure 6:
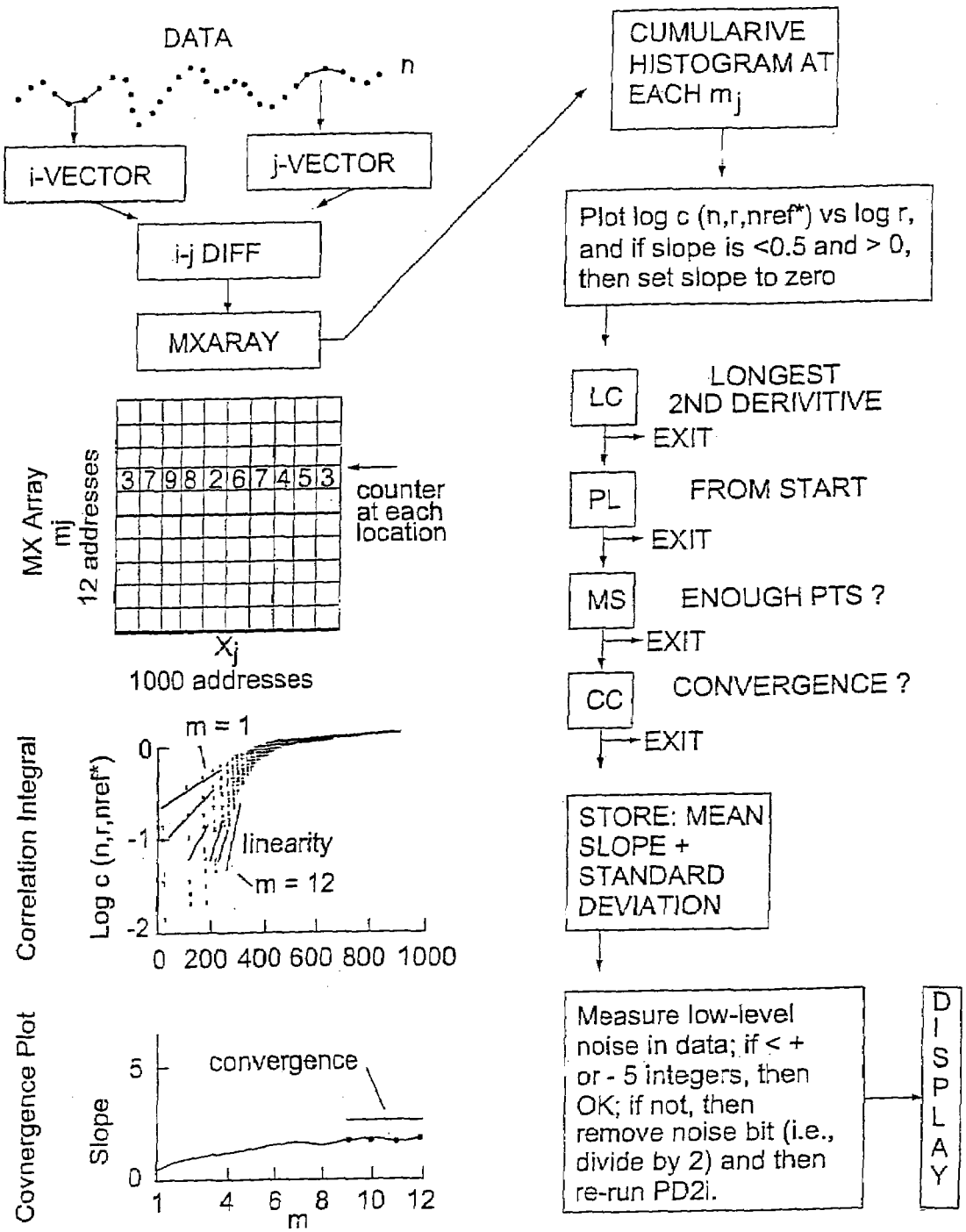
FIG. 6 illustrates exemplary flowcharts for the NCA implemented in software according to an exemplary embodiment.

FIG. 6 is a flow chart illustrating a process which the NCA may be implemented as software according to an exemplary embodiment. The flow begins with collection of the data. From the data, the i- and j-VECTORs are made and subtracted from one another (i-j DIFF). These vector difference lengths are entered, according the their value (X, 1 to 1000), into the MXARAY at the embedding dimension used (m, 1 to 12). The entry is made as an increment of a counter at each location of the MXARAY.

After completion of the making of the vector difference lengths, the counter numbers (3,7,9,8,2,6,7,4 . . . ) are then used to make the correlation integrals for each embedding dimension; this is done by making a cumulative histogram as a function of X, at each m.sub.1, and then making the log-log plot of their cumulative values (e.g., PLOT log C(n,r) vs log r). The cumulative histogram results in the log-log data plotted in the correlation integral for each embedding dimension (m).

The correlation integral is then tested for five criteria. First, it is determined whether the slope at each m is less than 0.5. If the slope is less than 0.5, it is set to zero. Next, the longest linear scaling region that is within the linearity criterion (LC) is found. This is accomplished by examining each correlation integral by the LC to find the longest segment of the second derivative that falls within the limits of the set parameter (LC=0.30 means within a + to − deviation of 15% of the mean slope); this iterative LC test will find a range above the "floppy tail" (i.e., the smallest log-r region that is unstable because of finite data length) and run up the correlation integral until the LC criterion is exceeded (bold section of top correlation integral).

Next, a determination is made whether the segment is within the plot length criterion (PL). If so, then the correlation integral scaling region is reset by the PL criterion; this value is set from the smallest data point in the correlation integral to its criterion value (e.g., 15%, bracket in second from top correlation integral). The upper and lower limits of this region are observed to see if they have at least the number of data points required by the minimum scaling (MS) criterion, e.g., 10. The selected regions of all correlation integrals (m−1 to m=12) are plotted and examined by the CC to see if convergence occurs at the higher embedding dimensions (e.g., m=9 to m=12); that is, to see if the selected regions have essentially the same slopes in which the standard deviation around the mean is within the limits set by the CC (.i.e., CC=0.40 means that the deviation around the mean is within + to −20% of the mean value). If the CC criterion is passed, then the mean slope and standard deviation are stored to file and, e.g., displayed.

Finally, the low-level noise is examined by the user to test if the dynamic range is outside the −5 to +5 interval. If so, then the noise bit is removed from the data file (i.e., each data point value is divided by 2), and the modified file is then re-calculated, displayed, and stored.

If failure occurs at any of the early criteria (LC, PL, MS) within the flow, then the program will exit and move the PD2i reference vector to the next data point and then start all over. If failure occurs at the CC, the mean and standard deviation are saved without exiting, for it may be the case that later the CC is desired to be changed; i.e., the CC is a filter that determines whether or not the PD2i (i.e., the mean slope of m=9 to m=12) will be plotted in later graphical routines.

EXAMPLES

The present applicant has studied the degrees of freedom in HRV and found in humans with heart transplants (4) that the heartbeat variation was very regular and hardly changed at all. The nonlinear analysis of the HRV in these transplant recipients indicated but 1.0 degree of freedom. In contrast, in normal subjects the variation was rich, with between 3 to 5 degrees of freedom. This result in the denervated heart suggests that it is the brain-projected neural activity to the heart that produces the HRV in the first place.

The nonlinear analysis of the heartbeat dynamics is a sensitive detector of underlying dynamics. It can clearly detect vulnerability to lethal arrhythmogenesis that other measures of HRV cannot (5). It can also detect alterations in the regulatory neurons when only the intrinsic cardiac nervous system is available to regulate the heartbeat intervals (6,7) or when higher cognitive systems involving the frontal lobes are involved (8).

HRV and Cognitive Function

The association of HRV and cognitive function and activity of daily living capacity in the elderly is not clear (9). The total power (i.e., LF and LF/HF ratio of the power spectrum) of HRV was found to be significantly lower in the dementia sub-group of the elderly subjects than in the normals (9). Therefore, it is not age per se that is related to the reduction in HRV. Rather, this result confirms the denervation study, which showed that it is the lack of higher neural activity projected to the heart that causes the HRV to diminish.

It is important to know at what point in progressive global neural challenge does the HRV actually begin to change. A change in the amplitude or oscillatory power of the variation, which comes with total neural involvement equivalent to descending nerve transsection, would be a late result and not very useful medically. Perhaps a more subtle change occurs early in the process that is picked up by a change in the degrees of freedom. It is quite likely that an early global challenge, as in the beginning stage of BSE and/or Alzheimer's disease, has an affect on a number of total neurons and thus the number of degrees of freedom of the HRV would become reduced significantly. If this is the case, then this nonlinear measure of HRV could be the harbinger of what is to result 10 years later in the disease process.

Figure 7:
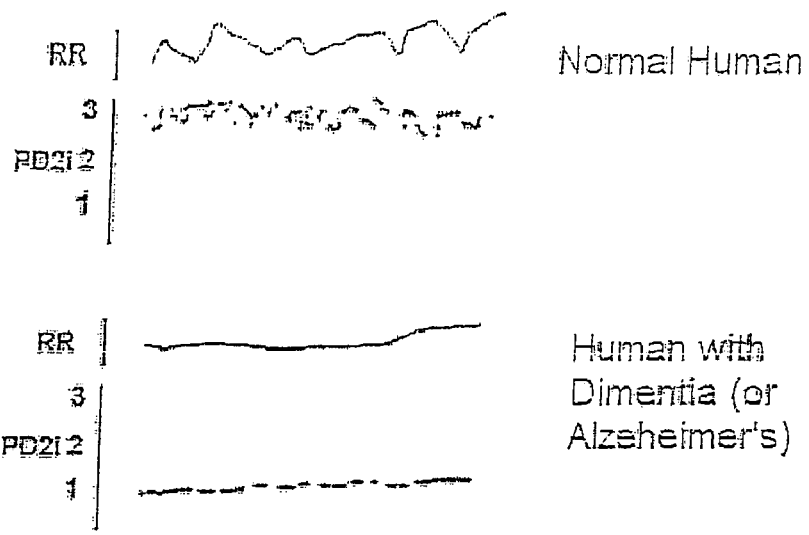
FIG. 7 illustrates the PD2i of the heartbeats (RR) of a person with early dementia that was not confirmed until 10 years later compared to that of an age-matched normal subject.

One elderly subject, SGW, was studied. This subject was in good health (played tennis 3 times per week) and was not cognitively impaired. Although this subject had some minor difficulties in the recall of remote names (e.g., authors of various published manuscripts), there certainly was no sign of other short-term or long-term memory loss, or any indication of dementia. The HRV of this subject, however, was quite reduced at the time, to a value ranging between 2.0 and 1.0 dimensions. This reduction in nonlinear dimension (degrees of freedom) was clearly not the case in age-matched controls whose values ranged between 5 and 3 in the same range as that of other younger, normal subjects. The difference in mean PD2i values between SGW and the age-matched normal was highly statistically significant (t-test, p<0.001). The most important observation in this 10-year study was that after 10 years had passed, this particular subject (SGW) manifested a severe loss of short-term memory and exhibited severe dementia (FIG. 7).

It is interpreted that tonic reduction in the degrees of freedom (dimension) of the HRV is a long-term predictor of the neural dementia to come. The same mechanism can be analogous for Bovine Spongioform Encephalitis detection in its early stages in cattle and similar prion diseases in humans (Jacob-Cruetzfeld Disease) that also take 10 years to develop.

The power spectra algorithm used to evaluate the HRV in previous studies presumes a linear stochastic model, which in turn requires that the variation in respiratory regulation be randomly distributed around a mean and be a stationary data series. Neither of these presumptions is valid in such physiological data series, as any behavior can interfere with respiration and produce nonlinear and non-stationary changes in the data.

Applicant has shown that a nonlinear algorithm, the Point Correlation Dimension (PD2i), which is based on a nonlinear deterministic model, addresses the problem of non-stationary data. It is able to accurately track the changes in the degrees of freedom of the variation in non-stationary data series (10). The power spectrum which was used in previous studies (1) requires data stationarity, and it was not likely to be present in the conscious behaving animals.

In application of the PD2i algorithm to clinical heart rate variability studies in high-risk cardiac patients, the PD2i algorithm was markedly superior in its predictability of arrhythmic death outcome compared to other algorithms commonly used in the field (11,12), including the power spectrum.

Figure 8:
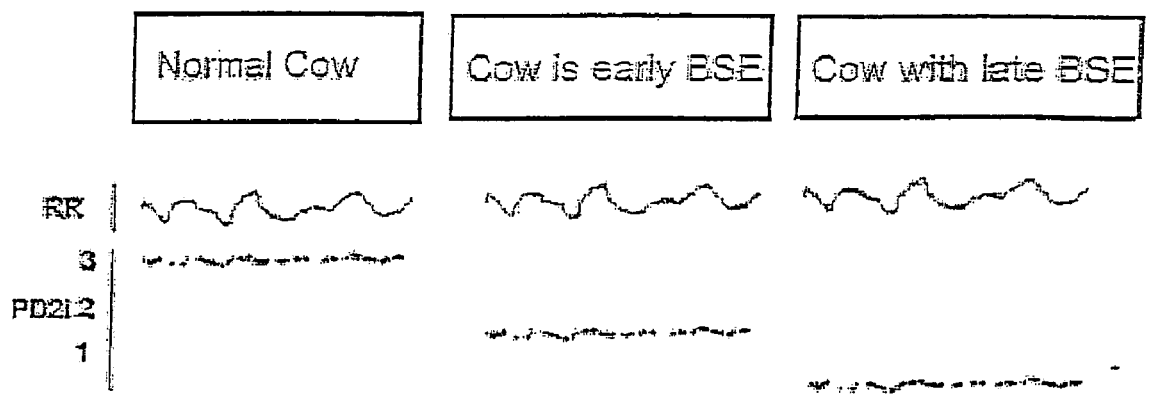
FIG. 8 illustrates the relationship of PD2i of the heartbeats (RR) in a cow with early and late stage bovine spongioform encephalitis (BSE).

The present invention shows that the PD2i reduction in the heartbeat variability in humans predicts progressive brain disorder in a case of cerebral dementia. This same nonlinear heartbeat measure can likewise predict progressive brain diseases in animals, especially cattle infected by bovine spongioform encephalitis. It has been shown that brain regulation of the heartbeats provides the higher dimensions of the PD2 (4). It is further disclosed that as the encephalitis progresses it can have a quantitative relationship with PD2i dimensional reduction (FIG. 8). The same predictability can be used for early stage detection of other widespread cerebral disorders in humans, including, but not limited to, human prion diseases (Jacob-Creutzfeld Disease) and the various dementias (cardiovascular, traumatic, genetic), including Alzheimer's Disease. The technology can also work in similar or equivalent diseases in animals, including but not limited to, bovine spongioform encephalitis, sheep scrapie, elk wasting disease.

The reason the heartbeat interval variation encodes the physiological pathology to the initial stage of a progressive global disorders is because it measures the "cooperativity" (10) of the various afferent-efferent loops that compete to control the heartbeats. These afferent-efferent loops go all the way from the intrinsic nervous system wholly contained in the heart (6,7) to those that loop through the frontal lobes (8). Thus, the technology samples all levels of the central nervous system as well as the peripheral nervous system in the autonomic regulation of the heartbeats.

The inherent precision of the PD2i algorithm in quantitatively describing changes in the HRV is the result of it being based on a nonlinear deterministic model and treating the problem of data non-stationarity.

While the invention has been described with reference to specific embodiments, modifications and variations of the invention may be constructed without departing from the scope of the invention. For example, although the NCA has been described in its application to a PD2i data series, it should be appreciated that the NCA may also be useful in reducing noise in other types of algorithms, e.g., D2, D2i, or any other predictive algorithm.

It should be understood that the foregoing description and accompanying drawings are by example only. A variety of modifications are envisioned that do not depart from the scope and spirit of the invention.

The above description is intended by way of example only and is not intended to limit the present invention in any way.

Throughout this application, various publications are cited. The disclosures of these publications in their entireties are hereby incorporated by reference into this application in order to more fully describe the state of the art. The publications disclosed are also individually and specifically incorporated by reference herein for the material contained in them that is discussed in the sentence in which the reference is relied upon.

CITATIONS

1. Pomfrett, C J D, Austin, A R, Bovine spongiform encephalopathy (BSE) disrupts heart rate variability (HRV). *J. Physiol.* 501:69P, 1997.
2. Austin A R, Pawson L, Meek S, Webster S. Abnormalities of heart rate and rhythm in bovine spongiform encephalopathy. *Vet Rec* 141(14):352-7, Oct. 5, 1997.
3. Braun U, Abgottspon S, Gubler E, Schweizer T. Decreased sedation by xylazine and high blood pressure in cows with BSE. *Vet Rec* 144(26):715-7, Jun. 26, 1999.
4. Meyer, M., Marconi, C., Ferretti, G., Fiocchi, R., Cerretelli, P., Skinner, J.E. Heart Rate Variability in the Human Transplanted Heart: Nonlinear Dynamics and QT-vs-RR-QT Alterations During Exercise Suggest a Return of Neurocardiac Regulation in Long-Term Recovery. *Integ. Physiol. Behav. Sci.* 31:289-305, 1996.
5. Skinner, J. E., Pratt, C. M., Vybiral, T. A reduction in the correlation dimension of heart beat intervals preceeds imminent ventricular fibrillation in human subjects. *Am. Heart J.*, 125(3):731-743, 1993.
6. Skinner, J. E., Nester, B. A., and Dalsey, W. C. Nonlinear dynamics of heart rate variability during experimental hemorrhage in ketamine-anesthetized rats. *Amer. J. Physiol.-Heart Circ. Physiol.*, 297:H1669-H1678, 2000.
7. J. E.; Wolf, S. G.; Kresh, J. Y.; Izrailtyn, I., Armour, J. A., Huang, M-He. Application of Chaos Theory to a Model Biological System: Evidence of Self-Organization in the Intrinsic Cardiac Nervous System. *Integ. Physiol. Behav. Sci.*, 31(2):122-146, 1996.
8. Skinner, J. E., and Reed, J. C. Blockade of a frontocortical-brainstem pathway prevents ventricular fibrillation of the ischemic heart in pigs. *Am. J. Physiol.*, 240: H156-H163, 1981.
9. Murakami S, Yamanaka T, Kubo Y, Wada T, Yano S, Nishimura Y, Shinagawa M, Matsubayashi K, Otsuka K, Ohkawa S, Kawata H. Heart rate variability analysis and neurobehavioral function in community-dwelling older people aged 75 or older. *Nippon Ronen Igakkai Zasshi;* 39(5):520-6, September 2002.
10. Skinner, J. E., Molnar, M. Event-related dimensional reductions of the primary auditory cortex of the conscious cat are revealed by new techniques for enhancing the nonlinear dimensional algorithms. *Int. J. Psychophysiol.*, 34:21-35, 1999.
11. Skinner J E, Pratt C M, Vybiral T (1993) A reduction in the correlation dimension of heart beat intervals precedes imminent ventricular fibrillation in human subjects. *Amer Heart* 125:731-743, 1993. Also see, Vybiral, T; Skinner, J E. The point correlation dimension of RR-intervals predicts sudden cardiac death among high-risk patients. Computers in Cardiology, 257-260, September 2002.

12. Skinner, J E, Zebrowski, J J, Kowalik, Z J. (1997) New nonlinear algorithms for analysis of heart rate variability: low-dimensional chaos predicts lethal arrhythmias. In, Mayer-Kress, G, Kantz, H, Kurths, J (Eds.) Nonlinear Techniques in Physiological Time Series Analysis, Springer, N.Y., 1-37.

What is claimed is:

1. A method of detecting or predicting a cerebral disorder, comprising the steps of:
   analyzing input biological or physical data using a data processing routine including a set of application parameters associated with biological data correlating with the cerebral disorder to produce a data series,
   to reduce noise in the data series determining whether a slope of the data series is smaller than a predetermined value;
   if the slope is less than a predetermined value, setting the slope to a predetermined number; and
   using the data series to detect or predict the onset of the cerebral disorder.

2. The method of claim 1, wherein the cerebral disorder is bovine spongioform encephalitis.

3. The method of claim 1, wherein the cerebral disorder is Alzheimer's disease.

4. The method of claim 1, wherein the data processing routine uses the following algorithm to produce a data series PD2i:

$$PD2i \subseteq \log C(n, r, nref^*)/\log r$$

where $\subseteq$ means scales as, C is the correlation integral for PD2i in which n equals the data length, r equals the scaling range, and nref* equals a location of the reference vector for estimating the scaling region slope of log C/log r in a restricted small log-r range that is devoid of the effects of non-stationary data.

5. The method of claim 1, wherein the predetermined value is approximately 0.5.

6. The method of claim 1, wherein the predetermined number is zero.

7. The method of claim 1, further comprising:
   determining a noise interval within the data series; and
   if the noise interval is within a predetermined range, dividing the data series by another predetermined number and repeating the step of analyzing to produce new values for the data series.

8. The method of claim 7, wherein the other predetermined number is two.

9. The method of claim 7, wherein the predetermined range is −x to +x, where x is any number.

10. The method of claim 9, wherein the predetermined range is −5 to +5.

11. The method of claim 1, wherein the input biological or physical data includes electrophysiological data.

12. A method of detecting or predicting cerebral disorder, comprising the steps of:
   analyzing input biological or physical data using a data processing routine including a set of application parameters associated with biological data correlating with the cerebral disorder to produce a data series;
   determining a noise interval within the data series; and
   if the noise interval is outside a predetermined range, dividing the data series by a predetermined number and repeating the step of analyzing to produce new values for the data series; or
   if the noise interval is within the predetermined range, using the data series to detect or predict the onset of cerebral disorder.

13. The method of claim 12, wherein the cerebral disorder is bovine spongioform encephalitis.

14. The method of claim 12, wherein the cerebral disorder is Alzheimer's disease.

15. The method of claim 12, wherein the data processing routine uses the following algorithm to produce a data series PD2i:

$$PD2i \subseteq \log C(n, r, nref^*)/\log r$$

where $\subseteq$ log means scales as, C is the correlation integral for PD2i in which n equals the data length, r equals the scaling range, and nref* equals a location of the reference vector for estimating the scaling region slope of log C/log r in a restricted small log-r range that is devoid of the effects of non-stationary data.

16. The method of claim 12, wherein the predetermined number is two.

17. The method of claim 12, wherein the predetermined range is −x to +x, where x is any number.

18. The method of claim 17, wherein the predetermined range is −5 to +5.

19. The method of claim 12, further comprising:
   determining whether a slope of the data series is smaller than a predetermined value; and
   if the slope is less than a predetermined value, setting the slope to another predetermined number.

20. The method of claim 19, wherein the predetermined value is approximately 0.5.

21. The method of claim 19, wherein the other predetermined number is zero.

22. The method of claim 12, wherein the biological or physical data includes electrophysiological data.

23. method of detecting or predicting a cerebral disorder selected from the group consisting of human prion diseases, cardiovascular dementia, traumatic dementia, and genetic dementia, the method comprising the steps of:
   analyzing input biological or physical data using a data processing routine including a set of application parameters associated with biological data correlating with the cerebral disorder to produce a data series;
   to reduce noise in the data series determining whether a slope of the data series is smaller than a predetermined value;
   if the slope is less than a predetermined value, setting the slope to a predetermined number; and
   using the data series to detect or predict the onset of the cerebral disorder.

24. The method of claim 23, wherein the data processing routine uses the following algorithm to produce a data series PD2i:

$$PD2i \subseteq \log C(n, r, nref^*)/\log r$$

where $\subseteq$ log means scales as, C is the correlation integral for PD2i in which n equals the data length, r equals the scaling range, and nref8 equals a location of the reference vector for estimating the scaling region slope of log C/log r in a restricted small log-r range that is devoid of the effects of non-stationary data.

25. The method of claim 24, further comprising:
   determining a noise interval within the data series; and
   if the noise interval is within a predetermined range, dividing the data series by another predetermined number and repeating the step of analyzing to produce new values for the data series.

* * * * *

UNITED STATES PATENT AND TRADEMARK OFFICE
CERTIFICATE OF CORRECTION

PATENT NO. : 7,276,026 B2  Page 1 of 1
APPLICATION NO. : 10/767861
DATED : October 2, 2007
INVENTOR(S) : James Skinner et al.

It is certified that error appears in the above-identified patent and that said Letters Patent is hereby corrected as shown below:

Title Pg, Item (75) Inventors: please include the following name as a co-inventor along with James Skinner:

-- Jerry Anchin, Boca Raton (FL) --

Signed and Sealed this

Twenty-third Day of September, 2008

JON W. DUDAS
*Director of the United States Patent and Trademark Office*